US005549598A

United States Patent [19]
O'Donnell, Jr.

[11] Patent Number: 5,549,598
[45] Date of Patent: Aug. 27, 1996

[54] GLAUCOMA LASER TRABECULODISSECTION

[76] Inventor: Francis E. O'Donnell, Jr., 709 The Hamptons La., Town & Country, Mo. 63017

[21] Appl. No.: 445,898

[22] Filed: May 22, 1995

[51] Int. Cl.⁶ ........................................... A61B 17/36
[52] U.S. Cl. ............................. 606/6; 606/10; 606/12
[58] Field of Search ........................ 606/2, 3–6, 10–13

[56] References Cited

U.S. PATENT DOCUMENTS 5,152,760 10/1992 Latina .................................. 606/6
5,222,952 6/1993 Loertscher ........................... 606/6
5,370,641 12/1994 O'Donnell, Jr. ..................... 606/4

Primary Examiner—David M. Shay
Attorney, Agent, or Firm—Paul M. Denk

[57] ABSTRACT

A method for performing a trabeculodissection comprising the steps of forming a scleral flap, determining the treatment arc of tissue located under the scleral flap, designating a number of discrete test areas along the treatment arc under the scleral flap, performing test ablations within the discrete test areas with a galvanometric scanning laser delivery system, determining the discrete treatment zones corresponding to the test areas, programming the galvanometric scanning laser delivery system based upon the results of the test ablations, ablating the tissue, and repairing the sclearal flap.

7 Claims, 1 Drawing Sheet

GLAUCOMA LASER TRABECULODISSECTION

BACKGROUND OF THE INVENTION

This invention relates generally to a method of controlling open-angle glaucoma by surgery and more specifically to the use of a laser in surgery to reduce the thickness of the trabecular meshwork and tissue around Schlemm's Canal to increase filtration of the aqueous humor and thereby controlling the open-angle glaucoma.

Primary open angle glaucoma is a disease of unknown etiology also known as simple glaucoma, chronic glaucoma, glaucoma simplex, compensated glaucoma, and open angle glaucoma. The disease is characterized by the increase in intraocular pressure which results in atrophy of the optic nerve, visual field disturbances, and eventual blindness. In primary open angle glaucoma the anterior chamber angle appears normal to direct observation and the aqueous humor has free access to the trabecular meshwork. Secondary open-angle glaucoma can occur because of fibrovascular proliferation and the trabecular meshwork is abnormal. Obstruction of the trabecular meshwork prevents the filtration of aqueous humor with a resulting increase in intraocular pressure.

Open angle glaucoma can be treated medically or surgically. The preferred treatment is medical and is directed to increasing the outflow of aqueous humor from the anterior chamber of the eyeball or by decreasing the secretion of aqueous humor, or both.

Primary open angle glaucoma can be treated with drugs such as timolol, an adrenergic receptor antagonist; pilocarpine, a cholinergic stimulating drug; echothiophate iodide, a cholinesterace antagonist; epinephrine, an alpha and beta agonist; and acetazolamide, a carbonic anhydrase inhibitor.

There are problems inherent with medical treatment. Miotic drugs, such as pilocarpine, may aggravate the visual loss caused by incipient cataract or may induce painful ciliary muscle spasms. Epinephrine may be irritating to the eye. Echothiophate iodide has a myriad of adverse effects, drug interactions and contraindications, as does acetazolamide. Timolol is contraindicated in patients with asthma and other pulmonary diseases.

If the glaucoma cannot be controlled by drugs and there is progress in the associated visual field disturbances and optic nerve atrophy, surgery is indicated.

The main surgical procedure used in the treatment of open angle glaucoma in which the trabecular meshwork is visible is laser trabeculoplasty, commonly using an argon laser. The eye is anesthetized and the trabecular meshwork is visualized through a gonioprism. The laser energy is applied ab externo to photocoagulate the trabecular meshwork. The laser can reduce the circumference of the trabecular ring by heat induced shrinkage of the collagen of the sheet of trabecular tissue or by scar tissue contraction at the burn sites, forcing the ring to move toward the center of the anterior chamber, elevating the sheets and pulling open the trabecular spaces. Flow is increased through the trabecular spaces. The main complication in this type of surgery is a transient increase in intraocular pressure that may require medication to control. Control is usually achieved in about 85% of all patients, but most (75%) continue to require some medication. Control can be lost, however, with the passing of time and additional laser trabeculoplasty may not be effective.

In eyes where laser trabeculoplasty cannot be performed or where it fails to control pressure, a filtering operation is indicated. All previous filtering operations were based on the theory of creating fistula between the anterior chamber and the sub-conjunctival space through which aqueous humor can flow. Generally, the surgery was performed by scalpel. Trabeculectomy is the operation of choice. An operating microscope is used and a scleral flap is fashioned to expose the trabecular meshwork. A portion of the full thickness eye wall is excised and the scleral flap replaced. A filtering bleb often develops after surgery. This surgery is performed in an operating suite and complications can include excessively low intraocular pressure, flat anterior chamber, endophthalmitis, cataract, sympathetic ophthalmic and bullous keratopathy. Furthermore, a mechanical deep dissection down to Sclemm's canal has limited success because of the difficulty in judging the depth of dissection of the trabecular meshwork and the surgeon can inadvertently enter the anterior chamber with the surgical tool.

Attempts to remedy the drawbacks associated with traditional trabeculectomy have had some success. My U.S. Pat. No. 5,370,641 discloses a method of performing laser trabeculodissection wherein laser energy is applied to the corneo scleral bed under a scleral flap, tissue is removed until sufficient aqueous humor is coming through the ultra-thin remaining Schlemm's Canal and trabecular meshwork. The energy of the laser is absorbed by the outflowing aqueous humor thereby creating a self-regulating endpoint. The scleral flap is replaced with or without a suture.

I have discovered that there is one notable drawback to the method disclosed in U.S. Pat. No. 5,370, 641. Laser trabeculodissection is performed with an ultraviolet wavelength wherein the wavelength is less than 230 nanometers. The ultraviolet wavelength is unsuitable for fiberoptic transmission. I have determined that the preferred embodiment is an ultraviolet laser that employs a galvanometric scanning delivery system rather than a variable aperture (iris-diaphragm) delivery system. Examples of the galvanometric scanning delivery systems include the COMPAK-200 Mini-Excimer and the LASERHARMONIC, both manufactured by LaserSight, Inc. (Orlando, Fla.).

The advantages of a galvanometric scanning delivery system are rooted in the anatomy of the portion of the eye to be treated and also in the programmable features of the system. As shown in FIG. 1, the anatomy of the portion of the limbal area to be treated is characterized by a curvilinear shape with a radius of approximately 7.5 mm. The arc length and width of treatment in the corneal scleral bed partially is determined by the severity of the glaucoma; the more severe glaucoma requires a broader and longer arc of trabeculodissection. The width is limited by the fact that the average maximum with of the trabecular meshwork is less than 1 mm. The arc is limited by the circumference of the limbal area around the eye.

Moreover, the trabecular meshwork is covered by an uneven amount of corneoscleral tissue. Specifically, the anterior-most portion near the scleral septum id deeper and thinner that is the posterior portion neat the scleral spur (iris root). The latter portion is more superficial and thicker. In addition, the ablation rate of corneal tissue is different from scleral tissue.

The goal of laser trabecular dissection is to achieve as wide an area (anteroposterior) as possible of partial thickness dissection over the trabecular meshwork, especially the posterior portion, sufficiently deep to allow for adequate aqueous drainage but not too deep that the dissection enters the anterior chamber, A galvanometric scanning delivery system (GSS) is ideally suited to meet the above objectives. Specifically, the laser is programmed for a low, but suprathreshold, fluence, typically less than 120 mJ/cm$^2$ to reduce the risk of full thickness penetration. The pulse frequency is set, typically at 60 to 300 Hertz, to achieve as rapid ablation as possible so as to reduce the potential for slow filtration that could absorb the laser energy and mask the laser effects. The GSS also allows selection of small spot size in the range to 100 to 300 microns.

Variable aperture delivery systems cannot be preprogrammed to achieve an appropriate ablation profile. The lack of a homogenous energy profile can create hot and cold spots and increase the risk of full perforation. Moreover, the attendant acoustic shockwave promotes premature drainage of aqueous that interferes with the ablation.

Furthermore, prior art laser trabeculodissection has an endpoint. When filtration begins, the aqueous humor absorbs the laser energy and masks the laser's effect. It would be beneficial, therefore, to use a method of surgery that allows filtration to proceed at one ablation site without interfering with the laser energy at a subsequent site.

OBJECTS OF THE INVENTION

It is among the several objects of the present invention to provide a method for using a galvanometric scanning delivery system to achieve trabeculodissection.

It is another object of the invention to provide a method of using a galvanometric scanning delivery system that provides a plurality of test zones across the width and length of the treatment arc so that the system can be programmed to provide the optimum level dissection across a treatment arc of variable thickness.

Yet anther object of the invention is to provide a such a method in which the ablations are performed in zones, based upon the results of the test zones, to obtain ablation without perforation.

Still another object of the present invention is to provide such a method that utilizes a relatively low fluence to reduce the risk of inadvertent full-thickness perforation into the anterior chamber.

Another object of the invention is to provide a method of performing a laser trabeculodissection that avoids acoustic shockwaves.

A still further object of the present invention is to provide such a method utilizing a laser system that has a homogenous energy profile, removes tissue in scan layers to produce zones of minimal thickness.

In accordance with the invention, generally stated, a method of performing trabeculodissection using a galvanometric scanning laser delivery system is provided. The surgeon uses a diamond knife and scleral dissector to fashion a scleral flap and expose the treatment arc of trabecular meshwork. The arc of the treatment area is as wide as the trabecular meshwork and the length of the arc is limited by the circumference of the limbal area around the patient's eye. The surgeon uses the laser to treat small test areas in successive discrete zones along the arc of the treatment area in the bed of the scleral flap to determine the precise depth of ablation required over each entire zone to promote filtration without penetration of the treatment zone. The laser then is programmed to treat the length of the arc in discrete zones. Tissue is removed in scan layers, typically 2 microns thick, so as to produce discrete ablated zones of minimal residual thickness. The treatment of successive zones allows ablation along the length of the treatment arc without interference from actively draining aqueous. After ablation of the various successive zones, the scleral flap is closed and, if necessary, sutured,

DESCRIPTION OF THE PREFERRED EMBODIMENT

Figure 1:
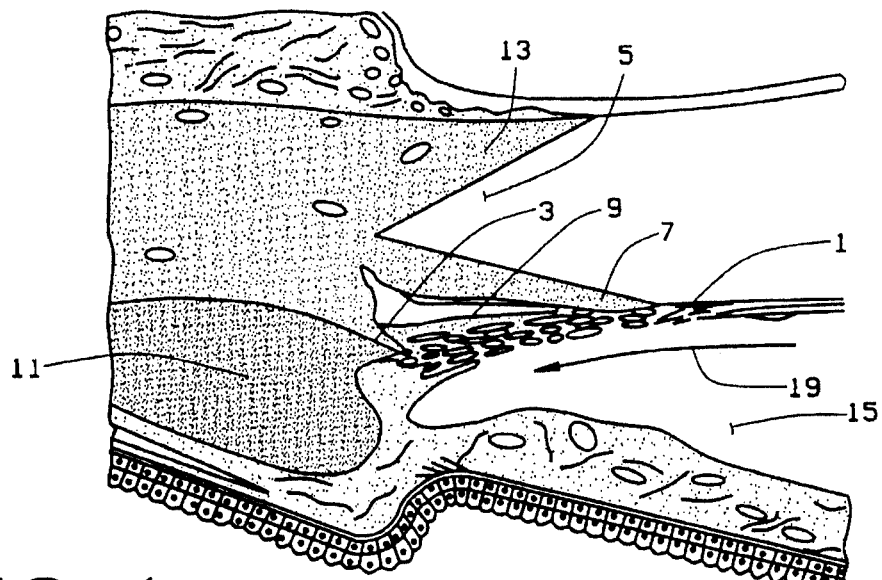
FIG. 1 is a partial cross section of a section of the eye illustrating the treatment area for the laser trabeculodissection of the present invention.

FIG. 1 generally illustrates the anatomical structures of the treatment area of the eye. The relevant structures include trabecular meshwork 1, the scleral spur 3, the cornea 5, the scleral septum 7, Schlemm's Canal 9, the ciliary muscle 11, the sclera 13, he conjunctiva 15, and the anterior chamber 17. It will be noted that the trabecular meshwork 1 increases in thickness from the tip of the scleral septum 7 toward the scleral spur 3 along arrow 19. This increase in thickness is due to an uneven amount of corneoscleral tissue covering of the trabecular meshwork 1. It will be appreciated, therefore, that a filtering trabeculodissection that involves a treatment arc that extends the length of arrow 19 requires ablation at different depths along arrow 19. Moreover, the ablation depth will vary depending on the variation in ablation rate of scleral as opposed to corneal tissue.

As stated above, the treatment area has a curvilinear shape with a radius of approximately 7.5 mm. The arc length and width are partially determined by the severity of the glaucoma, with more severe glaucoma necessitating a broader and longer arc of trabeculodissection. Again, the width is limited by the maximum with of the trabecular meshwork 1. In general, the width of trabecular meshwork 1 is less than 1.0 mm. The ablation must be sufficiently deep to allow for adequate drainage of aqueous but not so deep as to penetrate into anterior chamber 15.

Figure 2:
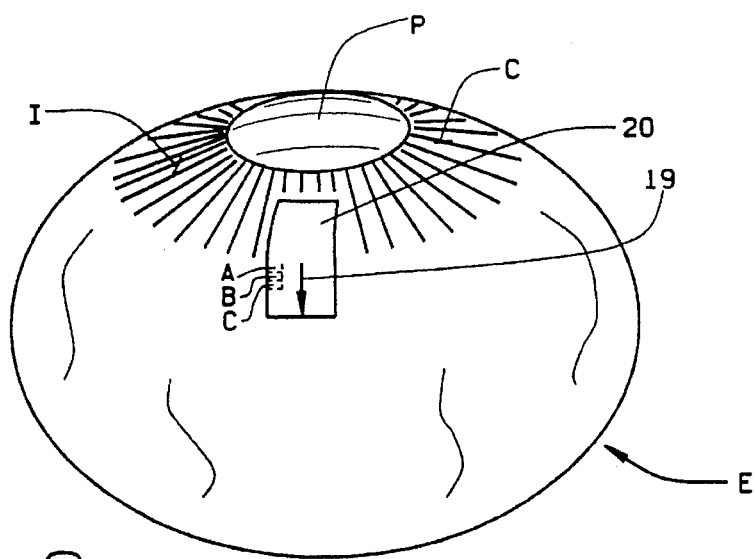
FIG. 2 is a partial, enlarged isometric view of the eye illustrating the test areas in the treatment zones.

FIG. 2 illustrates a test area 20 for the surgical method of the present invention. Test area 20 is formed through the surface of the eyeball E, as follows. The notable anatomic landmarks include the cornea C, iris I and pupil P. A diamond knife (not shown) is set for a blade extension of 400 microns. A incisions are made and a scleral flap 22 is made using a scleral dissector. The scleral flap is formed at the limbal juncture, approximately at the peripheral margin of iris I. The treatment area (See FIG. 1) under scleral flap 22 is exposed. The surgeon isolates three small distinct test areas A, B, and C along a treatment are that extend along arrow 19 which generally conforms to the treatment arc of arrow 19 described with reference to FIG. 1.

The test areas A through C are treated with a galvanometric scanning delivery system laser (not shown). The surgeon determines the appropriate depth of treatment in each discrete zone along treatment arc by the response of the smaller test areas A through C within the zones to the tiny test ablations.

Figure 3:
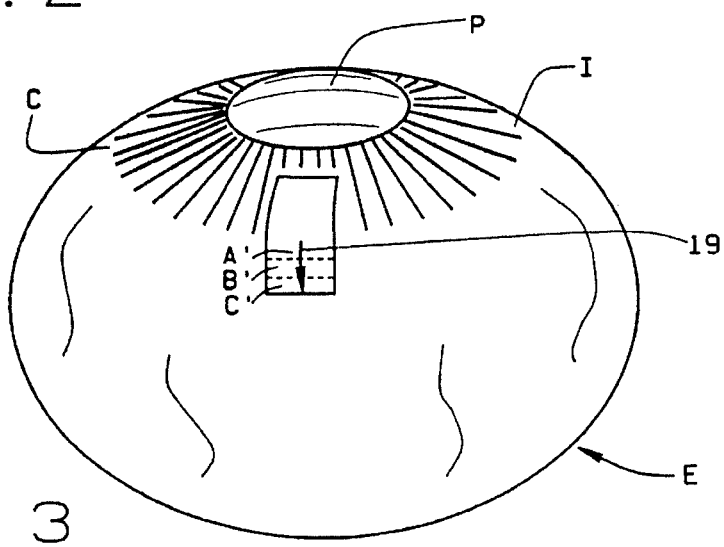
FIG. 3 is a partial, enlarged isometric view of the eye illustrating the method of the present invention applied to the treatment zones.

The laser then is programmed to treat the length of arc 19 beneath scleral flap 20, in discrete test areas A' through C', as shown in FIG. 3. As mentioned above, the laser is programmed based upon the response to the test ablations. Specifically, the laser is programmed for a low, but suprathreshold, fluence, less than 120 mJ/cm$^2$ to reduce the risk of full thickness penetration of the trabecular meshwork 1. The pulse frequency is set at 60 to 300 hertz to achieve as rapid ablation as possible and reduce the potential for slow filtration that could create and endpoint that masks the laser's effects. A small treatment spot size of 100 to 300 microns is used.

The treatment zones are ablated in scan layers, typically 2 microns thick so as to produce zones of minimal thickness with each zone having approximately equal residual depth. Each zone is treated separately and discretely so that any filtration that occurs through the prior treated zone remains isolated in that zone and does not interfere with or mask ablation in the next treated zone.

The programmed GSS provides a homogeneous energy profile that eliminates hot and cold spots and decreases the risk of full thickness perforation. Furthermore, the GSS system does not produce shockwaves.

Although the drawings illustrated three separate test zones, it will be appreciated that the number of test or treatment zones may vary depending upon the length of treatment arc 19.

It will be appreciated that various changes and modifications can be made in the method of the present invention without departing from the scope of the appended claims. Therefore, the foregoing description and accompanying drawings are intended to be illustrative only and should not be construed in a limiting sense.

What is claimed:

1. A method of performing trabeculodissection comprising performing a laser ablation in discrete treatment areas along a defined treatment arc of the trabecular meshwork to obtain equal residual depth along the treatment arc despite the fact that the trabecular meshwork varies in thickness along the length of the treatment arc.

2. The method of claim 1 wherein the step of ablating in discrete treatment areas includes preventing filtration through a previously ablated area from interfering with the ablation in a subsequent treatment area.

3. A method for performing a trabeculodissection comprising the steps of:

fashioning a scleral flap;

determining a treatment arc of tissue under the scleral flap;

designating a number of discrete test areas along the treatment arc under the scleral flap;

performing test ablations within the discrete test areas with a galvanometric scanning laser delivery system;

evaluating the test ablations;

designating a number of discrete treatment zones corresponding to the discrete test areas along the treatment arc;

programming the galvanometric scanning laser delivery system based upon the results of the test ablations;

ablating the tissue in the discrete treatment zones to a sufficient depth to allow for adequate drainage of aqueous humor; and repairing the scleral flap.

4. The method of claim 3 wherein the step of fashioning includes fashioning the scleral flap with a diamond knife with a blade extension of 400 microns.

5. The method of claim 3 wherein the step of programming includes programming the galvanometric scanning laser delivery system for a low but suprathreshold fluence.

6. The method of claim 5 wherein the step of programming the low but suprathreshold fluence further comprises the step of programming the fluence to be less than 120 mJ/cm$^2$ to reduce a risk of full thickness penetration.

7. The method of claim 6 further includes the step of setting the pulse frequency between 60 to 300 hertz.

* * * * *